(12) United States Patent
Bogner et al.

(10) Patent No.: US 9,619,721 B2
(45) Date of Patent: Apr. 11, 2017

(54) MONITORING A DEGREE OF ATTENTION OF A DRIVER OF A VEHICLE

(71) Applicants: VOLKSWAGEN AG, Wolfsburg (DE); AUDI AG, Ingolstadt (DE)

(72) Inventors: Nico Bogner, Ehra-Lessien (DE); Gordon Großkopf, Ingolstadt (DE); Andreas Zachmayer, Abensberg (DE); Robert Büthorn, Berlin (DE); Stefan Brosig, Hankensbüttel (DE); Hendrik Franke, Braunschweig (DE); Asem Eltaher, San Leandro, CA (US)

(73) Assignees: Volkswagen AG, Wolfsburg (DE); Audi AG, Ingolstadt (DE)

( * ) Notice: Subject to any disclaimer, the term of this patent is extended or adjusted under 35 U.S.C. 154(b) by 0 days.

(21) Appl. No.: 14/882,681

(22) Filed: Oct. 14, 2015

(65) Prior Publication Data

US 2016/0104050 A1    Apr. 14, 2016

(30) Foreign Application Priority Data

Oct. 14, 2014  (DE) .................. 10 2014 220 759

(51) Int. Cl.
*G06F 7/70*     (2006.01)
*G06K 9/00*     (2006.01)
(Continued)

(52) U.S. Cl.
CPC ........ *G06K 9/00845* (2013.01); *A61B 5/1103* (2013.01); *A61B 5/18* (2013.01); *A61B 5/6893* (2013.01); *B60Q 9/00* (2013.01); *B60T 7/12* (2013.01); *B60T 7/14* (2013.01); *B60T 8/172* (2013.01); *B60W 30/12* (2013.01); *B62D 15/02* (2013.01); *B62D 15/021* (2013.01); *G06K 9/00604* (2013.01); *G06K 9/00798* (2013.01); *G08B 21/06* (2013.01); *A61B 5/0077* (2013.01); *B60T 2220/02* (2013.01); *B60T 2270/413* (2013.01)

(58) Field of Classification Search
USPC .......................... 701/70; 382/117; 600/558
See application file for complete search history.

(56) References Cited

U.S. PATENT DOCUMENTS 5,570,698 A * 11/1996 Liang .................... A61B 3/113
                                                340/575
5,867,587 A *  2/1999 Aboutalib ............. G08B 21/06
                                                340/576
(Continued)

FOREIGN PATENT DOCUMENTS

DE         10223210 A1   12/2003
DE    102005017242 A1   10/2006
(Continued)

OTHER PUBLICATIONS

Office Action for German Patent Application No. 10 2014 220 759.2; Feb. 10, 2015.

*Primary Examiner* — Thomas G Black
*Assistant Examiner* — Tyler Paige
(74) *Attorney, Agent, or Firm* — Barnes & Thornburg LLP

(57) ABSTRACT

To monitor a degree of attentiveness for a driver of a vehicle, a period is determined on the basis of a speed of the vehicle. It is determined whether an eyelid closed time and/or an eyelid closing time of the driver exceeds the period.

10 Claims, 4 Drawing Sheets

(51) Int. Cl.
*A61B 13/00* (2006.01)
*B62D 15/02* (2006.01)
*B60Q 9/00* (2006.01)
*B60T 7/12* (2006.01)
*B60W 30/12* (2006.01)
*G08B 21/06* (2006.01)
*A61B 5/18* (2006.01)
*A61B 5/11* (2006.01)
*B60T 7/14* (2006.01)
*B60T 8/172* (2006.01)
*A61B 5/00* (2006.01)

(56) References Cited

U.S. PATENT DOCUMENTS

| | | | |
|---|---|---|---|
| 6,163,281 A | 12/2000 | Torch | |
| 6,717,518 B1* | 4/2004 | Pirim | B60R 1/04 340/576 |
| 7,027,621 B1* | 4/2006 | Prokoski | G06K 9/00255 180/272 |
| 8,725,311 B1* | 5/2014 | Breed | G08B 21/06 600/300 |
| 9,135,803 B1* | 9/2015 | Fields | B60K 28/066 |
| 9,283,847 B2* | 3/2016 | Riley, Sr. | B60K 28/066 |
| 2006/0208169 A1* | 9/2006 | Breed | B60N 2/002 250/221 |
| 2006/0212202 A1* | 9/2006 | Ota | G08B 21/06 701/49 |
| 2009/0027212 A1 | 1/2009 | Nakagoshi et al. | |
| 2009/0091435 A1* | 4/2009 | Bolourchi | B60K 28/066 340/435 |
| 2009/0268022 A1* | 10/2009 | Omi | G08B 21/06 348/135 |
| 2010/0036290 A1* | 2/2010 | Noguchi | A61B 5/7267 600/595 |
| 2010/0090839 A1* | 4/2010 | Omi | B60K 28/04 340/575 |
| 2010/0214087 A1 | 8/2010 | Nakagoshi et al. | |
| 2011/0021866 A1* | 1/2011 | Iizuka | A61B 3/113 600/26 |
| 2012/0002843 A1* | 1/2012 | Yoda | A61B 5/1103 382/103 |
| 2012/0212353 A1 | 8/2012 | Fung et al. | |
| 2013/0073115 A1 | 3/2013 | Levin et al. | |
| 2014/0078281 A1* | 3/2014 | Tsou | G08B 21/06 348/78 |
| 2014/0172467 A1* | 6/2014 | He | B60K 28/066 705/4 |
| 2014/0210625 A1 | 7/2014 | Nemat-Nasser | |
| 2014/0276090 A1 | 9/2014 | Breed | |
| 2015/0314681 A1* | 11/2015 | Riley, Sr. | B60K 28/066 340/576 |

FOREIGN PATENT DOCUMENTS

| | | |
|---|---|---|
| DE | 102005057267 A1 | 6/2007 |
| DE | 102007060696 A1 | 8/2008 |
| DE | 102008007149 A1 | 10/2008 |
| DE | 102008056593 A1 | 5/2010 |
| DE | 102012001741 A1 | 8/2013 |
| DE | 102012100698 A1 | 8/2013 |

* cited by examiner

MONITORING A DEGREE OF ATTENTION OF A DRIVER OF A VEHICLE

PRIORITY CLAIM

This patent application claims priority to German Patent Application No. 10 2014 220 759.2, filed 14 Oct. 2014, the disclosure of which is incorporated herein by reference in its entirety.

SUMMARY

Illustrative embodiments relate to a method for monitoring a degree of attentiveness for a driver of a vehicle and to a corresponding apparatus. Illustrative embodiments relate, particularly, to techniques that involve determining whether an eyelid closed time of the driver exceeds a period.

BRIEF DESCRIPTION OF THE DRAWINGS

Illustrative embodiments are described in detail with reference to the attached drawings. In the drawings.

DETAILED DESCRIPTION OF THE DISCLOSED EMBODIMENTS

Figure 1:
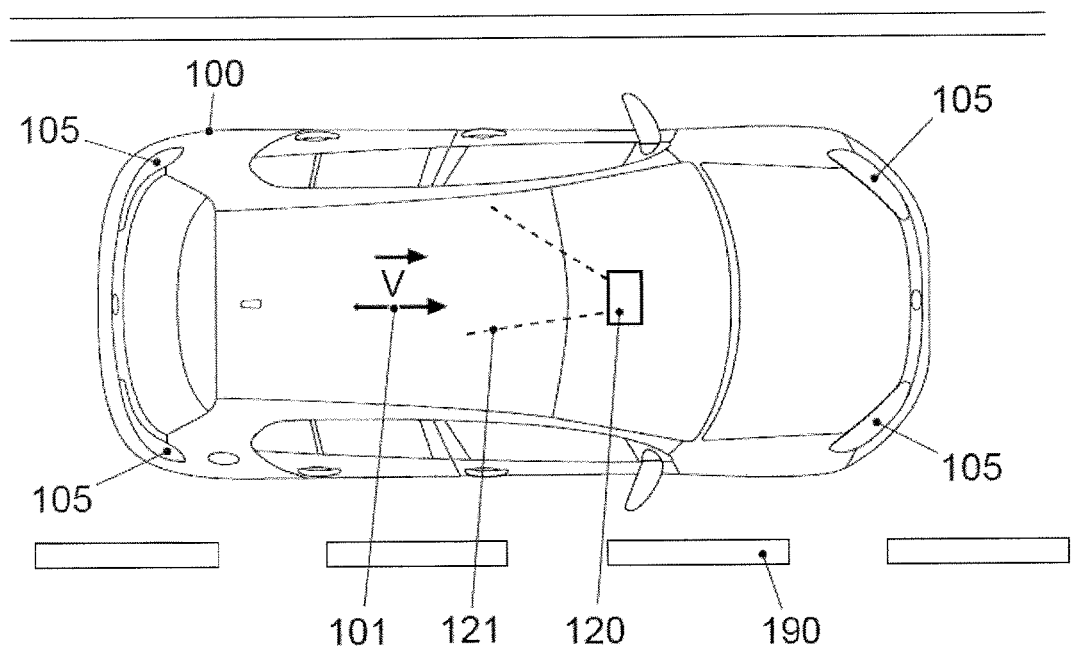
FIG. 1 is a plan view of a vehicle that comprises an interior camera for providing image data that depict a portion of the face of the driver.

A first disclosed embodiment relates to a method for monitoring a degree of attentiveness for a driver of a vehicle. The method comprises determination of a period, on the basis of a speed of the vehicle. The method additionally comprises reception of image data that depict a portion of the face of the driver. The method additionally comprises taking the image data as a basis for determining whether a blink time of the driver exceeds the period. The method also comprises monitoring of the degree of attentiveness of the driver on the basis of the determination of whether the blink time exceeds the period.

The blink time can relate, for example, to the lid closed time. Alternatively or additionally, the blink time can denote a period between the open and closed states or the closed and open of the eye (eyelid closing time). The eyelid closing time can thus denote the period that is required for changing the state of the eyelid.

The degree of attentiveness of the driver can denote an ability of the driver to perceive a journey situation in which the vehicle finds itself in a manner appropriate to the situation. The monitoring of the degree of attentiveness can mean that one or more variables quantifying the degree of attentiveness are determined continuously or at regular intervals of time and this variable is compared, for example, with a prescribed threshold value. It is then possible to establish for each monitoring process, or in a manner averaged over a plurality of monitoring processes, whether the degree of attentiveness is still adequate.

If a reduced degree of attentiveness is detected, further actions can be initiated. Further actions may be the output of a warning to the driver and/or the output of a warning to other road users and/or the initiation of a driver assistance action from a driver assistance system.

The period can be determined on the basis of a prescribed link between the speed of the vehicle and the period. A longer (shorter) period can be determined for lower (higher) speeds. In other words, it is possible for the period to be determined in a manner inversely proportional to the speed of the vehicle. Typical ranges for the period may be 50 ms to 2 s, preferably 150 ms to 800 ms.

The image data can be obtained from an interior camera of the vehicle. the interior camera may be fitted in the region of an upper part of a windshield of the vehicle and positioned and oriented such that its field of view covers at least a head region of the driver. The image data can comprise single frames or a film. In other words, it may be possible to determine the blink time with a higher or lower accuracy, depending on the magnitude of an interval of time between successive image data that depict the portion of the face of the driver at different times. It may then be possible to use techniques for image evaluation to identify the eyes of the driver in the image data and additionally to determine whether the eyelid of the driver is open or closed. If, in addition, various image data are implicitly or explicitly provided with a time stamp, this allows the blink time of the driver to be ascertained. It is then possible to perform a threshold value comparison between the period and the ascertained blink time and to deter dine whether the blink time of the driver exceeds the period.

If the blink time of the driver does exceed the period, it can be assumed that the degree of attentiveness of the driver is reduced. It may then be possible to output a warning and/or to initiate the driver assistance action. The warning can be sent to the driver and/or other road users.

The techniques described above can be used to achieve the effect of particularly situation-concordant monitoring of the degree of attentiveness of the driver. It would be possible, at comparatively low speeds, to tolerate a longer blink time—through appropriate determination of the period; at comparatively high speeds, however, the same blink time can result in a reduced degree of attentiveness of the driver being assumed.

Techniques have been explained above that involve the period that is compared with the blink time being determined on the basis of the speed of the vehicle. However, it would be possible for further factors to be considered for determining the period.

The method could additionally include a control signal that describes at least one from a journey situation parameter for a journey situation in which the driver finds himself, a steering parameter for steering and a lane parameter for the vehicle.

The journey situation parameter can describe, for example, current circumstances for a vehicle environment. Alternatively or additionally, the journey situation parameter may be indicative of the journey profile to date, that is to say may describe a progression or a profile for circumstances of the journey; this can take place on an integrated or time-resolved basis. The parameter can relate to one or more circumstances of the journey.

The journey situation parameter could be selected from the following group: a driving time; a time of day; an initiation frequency for a driver assistance system; a frequency for a change in the speed of the vehicle; a frequency for operation of pedals of the vehicle; and an ambient brightness. It is also possible for further or other journey situation parameters to be considered.

It would be possible for the steering parameter to be selected from the following group: an accuracy with which the driver follows a lane; a time characteristic for operation of the steering of the vehicle; a steering angle; a characteristic for the steering angle; a steering angle speed; a steering torque.

It is possible for the lane parameter to be selected from the following group: a time before a lane marker is crossed; and a distance to a lane marker.

The journey situation parameter and/or the steering parameter and/or the lane parameter may themselves be indicative of the degree of attentiveness, see German Patent Applications DE 10 2012 001 741 A1 and DE 10 2005 057 267 A1. In this way, it may be possible first of all to determine an intermediate degree of attentiveness or an indicator of tiredness (tiredness identification) on the basis of the journey situation parameter and/or the steering parameter and/or the lane parameter; this could then be conditioned by considering the comparison of the blink time with the period. In this way, it is possible to achieve particularly accurate and reliable monitoring of the degree of attentiveness.

Techniques have been described above that allow a reduced degree of attentiveness of the driver to be detected comparatively accurately and in a manner concordant with the situation. When such a reduced degree of attentiveness is detected, the driver can be warned. This can prompt the driver to restore attentiveness that is appropriate to the journey situation.

When a reduced degree of attentiveness of the driver is identified, the method can additionally comprise output of an audible warning and/or a haptic warning to the driver. The audible warning and the haptic warning may in particular be suitable for restoring a situation-concordant degree of attentiveness of the driver, that is to say for waking up the driver. The haptic warning could comprise brief tightening of a safety belt in the vehicle and/or brief operation of a brake of the vehicle and/or shaking of the steering wheel. The audible warning could comprise the output of a warning signal via loudspeakers in the vehicle.

It is also possible for a driver assistance action from a driver assistance system in the vehicle to be initiated when the result of the monitoring is a reduced degree of attentiveness. In this way, it is possible to achieve a reduction in a threat of the driver and/or other road users as a result of the journey situation. The driver assistance action can be selected from the following group: lateral guidance of the vehicle to follow a lane; lateral guidance of the vehicle to reach a breakdown lane; braking of the vehicle and operation of hazard lights of the vehicle.

The techniques described herein can also be used to allow cases of a particularly greatly reduced degree of attentiveness to be detected and suitable countermeasures to be taken. There may be a particularly greatly reduced degree of attentiveness of the driver in the case of a microsleep. Microsleep can occur when the driver falls into a sleep-like state while operating the vehicle. During microsleep, the blink time, particularly the eyelid closed time, of the driver becomes particularly long. Accordingly, the method could additionally comprise: monitoring of whether the reduced degree of attentiveness of the driver persists for a prescribed period.

The driver assistance action could be initiated when the reduced degree of attentiveness of the driver persists for the prescribed further period. In particular, the method could comprise: taking the image data as a basis for determining whether the blink time of the driver exceeds the prescribed further period; taking the determination of whether the blink time of the driver exceeds the prescribed further period as a basis for selective initiation of the driver assistance action. In other words, the driver assistance action can be selectively initiated if a situation-concordant degree of attentiveness of the driver is not restored even after a visual warning and/or a haptic warning. When the driver is in a microsleep, i.e. does not open his eyes again even after a warning is given, it may be necessary to take suitable measures to avoid an accident by initiating the driver assistance action. The prescribed further period could be of the same order of magnitude as the period that is determined on the basis of the speed of the vehicle. Alternatively, it would also be possible for the prescribed further period to be longer than the period. The prescribed period could be in the region of a few seconds.

In general, it may be possible to initiate one or more driver assistance actions. This can take place progressively. The method could additionally comprise successive initiation of at least two driver assistance actions when the reduced degree of attentiveness persists. Driver assistance actions that correspond to relatively little intervention (relatively great intervention) in the operating parameters of the vehicle can be initiated earlier (later) in relation to the initial identification of a reduced degree of attentiveness of the driver. In this way, the driver assistance actions can be initiated in a manner concordant with the situation; excessively great intervention right at the beginning of an identified reduced degree of attentiveness can be avoided.

A further disclosed embodiment relates to a controller that is set up to monitor a degree of attention for a driver of a vehicle. The controller comprises an interface. The interface is set up to receive image data that depict a portion of the face of the driver. The controller additionally comprises a computation unit. The computation unit is set up to determine a period on the basis of a speed of the vehicle. The computation unit is additionally set up to take the image data as a basis for determining whether a blink time of the driver exceeds the period. The computation unit is additionally set up to monitor the degree of attentiveness of the driver on the basis of the determination of whether the blink time exceeds the period.

The controller may be set up to carry out the method for monitoring the degree of attentiveness according to a further disclosed embodiment.

For such a controller according to the aspect discussed at present, effects can be achieved that are comparable with the method for monitoring the degree of attentiveness according to a further disclosed embodiment.

A further disclosed embodiment relates to a vehicle that comprises a controller that is set up to monitor the degree of attentiveness of a driver, according to a further disclosed embodiment. The vehicle may be an automobile or a commercial motor vehicle.

A further disclosed embodiment relates to a method for monitoring a degree of attentiveness of a driver of a vehicle. The method comprises determination of the degree of attentiveness of the driver on the basis of at least one from a blink time of the driver, a journey situation parameter, a steering parameter and/or a lane parameter. The method additionally comprises, on the basis of the determined degree of attentiveness: selective initiation of a warning to the driver. The method additionally comprises, when the reduced degree of attentiveness of the driver persists for a prescribed period following the output of the warning: initiation of a driver assistance action from a driver assistance system of the vehicle.

In other words, the warning to the driver to restore a situation-concordant degree of attentiveness can be initiated progressively in relation to the initiation of the driver assistance action. First of all, the initiation of the warning of the driver can attempt to restore an unreduced degree of attentiveness of the driver. If this measure is not successful, a second step can involve initiation of the driver assistance action from the driver assistance system in order to achieve a reduction in a criticality of the journey situation by means of suitable countermeasures. This can be accomplished by waiting for the prescribed period; if the degree of attentiveness of the driver has then not been restored in a manner concordant with the situation, it is possible to assume a microsleep.

The degree of attentiveness could be determined on the basis of the blink time of the driver and the journey situation parameter and the steering parameter and the lane parameter. In this way, the degree of attentiveness could be determined particularly accurately; in particular, monitoring of the blink time allows microsleep to be identified. The degree of attentiveness can be determined by using techniques that have been discussed above in relation to further disclosed embodiments. Accordingly, the warning can be an audible and/or haptic warning. Various driver assistance actions have been illustrated above; corresponding techniques can also be used according to the aspect discussed at present.

A further disclosed embodiment relates to a method for monitoring a degree of attentiveness for a driver of a vehicle. The method comprises determination of the degree of attentiveness of the driver on the basis of at least one from a blink time of the driver, a journey situation parameter, a steering parameter and a lane parameter. When a reduced degree of attentiveness is determined, the method can additionally comprise: successive initiation of the following actions while the reduced degree of attentiveness persists: initiation of a driver assistance action for lateral guidance of the vehicle to follow a lane; then initiation of a haptic warning to the driver; then initiation of a visual warning to other road users; then initiation of a braking process for the vehicle.

The driver assistance action for lateral guidance of the vehicle can be performed according to a lane departure warning system. The effect that can be achieved by this is that the vehicle follows the lane in which it currently finds itself. Departure from the lane may be less likely in this way. The haptic warning can comprise, as illustrated above in relation to further disclosed embodiments, in brief tightening of a safety belt in the vehicle, and/or a brake jolt. The visual warning to other road users can be achieved by operating a hazard light system of the vehicle.

In other words, it is thus possible for various actions, such as warning actions and driver assistance functions, to be initiated progressively while the reduced degree of attentiveness persists.

The features set out above and features that are described below can be used not only in the relevant explicitly presented combinations but also in other combinations or in isolation without departing from the scope of protection of the disclosed embodiments.

The disclosed embodiments are explained in more detail below with reference to the drawings. In the figures, the same reference symbols denote elements that are the same or similar. The figures are schematic representations of various embodiments. Elements shown in the figures are not necessarily shown to scale. Rather, the various elements shown in the figures are reproduced such that their operation and general purpose become comprehensible to a person skilled in the art. Connections and couplings that are shown in the figures between functional units and elements can also be implemented as indirect connection or coupling. A connection or coupling may be implemented on a wired or wireless basis. Functional units can be implemented as hardware, software or a combination of hardware and software.

Techniques for monitoring a degree of attentiveness for a driver of a vehicle are illustrated below. These techniques comprise determination of a period on the basis of a speed of the vehicle. This period is compared with a blink time of the driver. When the blink time exceeds the period, a reduced degree of attentiveness of the driver can be assumed. If the state of the closed eyelid persists, a particularly reduced degree of attentiveness of the driver can be assumed that can be referred to as microsleep.

In this case, the blink time can denote an eyelid closed time, that is to say a period of time for which the eyelid of the driver is in a closed state. However, it would alternatively or additionally also be possible for the blink time to denote an eyelid closing time, i.e. a period of time that the eyelid requires for changing between the open and closed states. In one implementation, it would be possible to monitor just the eyelid closed time or the eyelid closing time. In a further implementation, it would be possible to monitor both the eyelid closed time and the eyelid closing time. In that case, the degree of attentiveness can be determined particularly accurately. The method could comprise: determination of a first period on the basis of the speed of the vehicle; and determination of a second period on the basis of the speed of the vehicle; and taking the image data as a basis for determining whether the eyelid closed time of the driver exceeds the first period; and taking the image data as a basis for determining whether the eyelid closing time of the driver exceeds the second period; and monitoring of the degree of attentiveness of the driver on the basis of the determination of whether the eyelid closed time exceeds the first period, and additionally on the basis of the determination of whether the eyelid closing time exceeds the second period.

Given a reduced degree of attentiveness, suitable countermeasures may include a driver warning and/or an environment warning to other road users and/or initiation of driver assistance actions can be initiated. In particular, it may be possible for the warning and the initiation of the driver assistance action to be performed progressively in relation to the occurrence of the reduced degree of attentiveness.

The effect that can be achieved by considering the speed of the vehicle when determining the period is that it is monitored whether the degree of attentiveness is appropriate to the journey situation.

FIG. 1 shows an automobile 100 that moves along a lane 190 at a speed 101. The automobile 100 comprises an interior camera 120 that is mounted in the upper region of a front windshield of the automobile 100. FIG. 1 additionally illustrates a field of view of the interior camera 120 (shown in FIG. 1 by a dashed line). The field of view 121 is particularly oriented such that a portion of the face of the driver is depicted in image data captured by the interior camera 120.

Figure 2:
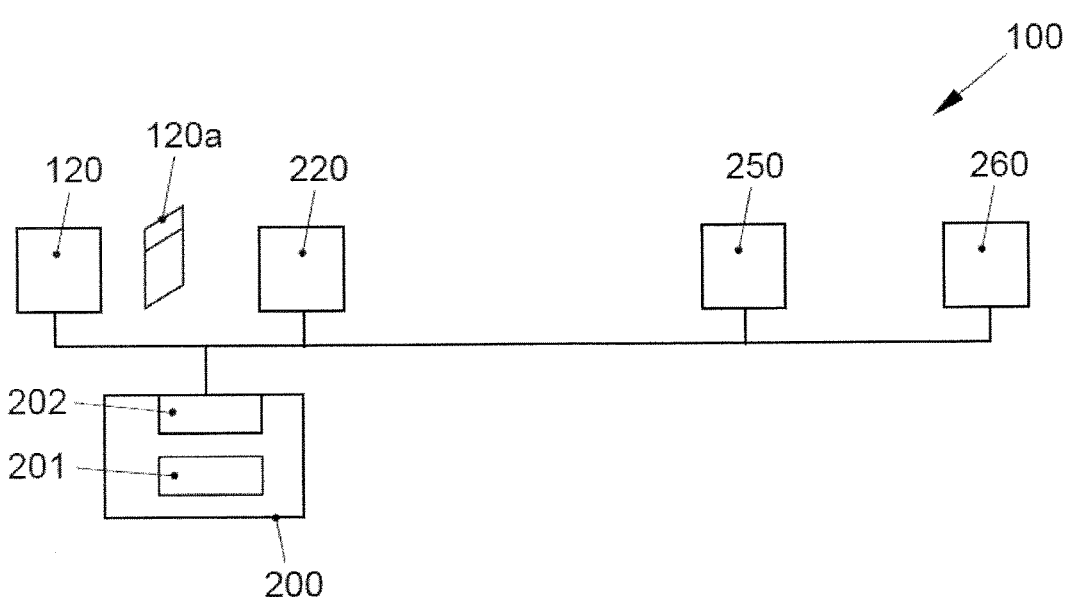
FIG. 2 is a schematic view of a controller that has a data link to further components of the vehicle and the interior camera and is set up to monitor a degree of attentiveness of the driver according to disclosed embodiments.

These image data 120a are transmitted from the interior camera 120 to a controller 200 (see FIG. 2). To this end, the controller 200 comprises an appropriately set-up interface 202. The image data could be transmitted between the interior camera 120 and the controller 200 via a vehicle bus system. The controller 200 additionally comprises a computation unit 201. The computation unit 201 is set up to take the image data as a basis for determining whether an eyelid closed time of the driver exceeds a period.

The blink time is primarily referred to as eyelid closed time below. The techniques described below can also be applied directly to the eyelid closing time, however. Typically, the period that is compared with the eyelid closing time may be shorter than the period with which the eyelid closed time is compared.

This period is determined by the computation unit 201 on the basis of the speed 101 of the automobile 100. The period could be determined to be shorter (longer) for higher (lower) speeds 101. If the result of the comparison between the eyelid closed time and the period is that the eyelid closed time exceeds the period, a reduced degree of attentiveness of the driver can be assumed. In that case, appropriate countermeasures can be taken. The automobile 100 comprises a driver warning device 250. The driver warning device 250 is set up to output a visual warning and a haptic warning to the driver. The effect that can be achieved by this is that an unreduced and situation-concordant degree of attentiveness of the driver is restored. In addition, it would be possible for other road users to be warned by operating hazard lights 105 (cf. FIG. 1) of the automobile 100. The automobile 100 additionally comprises a driver assistance system 260. When a reduced degree of attentiveness of the driver is identified, a driver assistance action for the driver assistance system 260 can be initiated. The driver assistance action could be selected from the following group: lateral guidance of the automobile 100 to follow the lane 190; lateral guidance of the automobile 100 to reach a breakdown lane; braking of the automobile 100; operation of the hazard lights 105 of the automobile 100.

In one simple implementation, it would be possible for the control unit 200 to send appropriate control signals to the driver warning device 250 of the driver assistance system 260 simultaneously following identification of the reduced degree of attentiveness of the driver. The effect that can be achieved by this is particularly fast restoration of the unreduced situation-concordant degree of attentiveness of the driver and alleviation of a criticality of the journey situation of the automobile 100.

Alternatively, it would also be possible for first of all the warning to the driver to be given by the driver warning device 250. The driver assistance action can be initiated selectively when despite the warning the reduced degree of attentiveness of the driver persists for a prescribed further period. In particular, it would be possible to check, following the warning to the driver, whether his eyelid continues to be closed—this can indicate a particularly reduced degree of attentiveness such as a microsleep. In other words, the warning and the driver assistance action can thus be initiated progressively.

Alternatively or additionally, it is also possible for the various driver assistance actions and the warning to be initiated as a mixture and progressively if the reduced degree of attentiveness of the driver persists. It would first of all be possible to initiate a driver assistance action for lateral guidance of the vehicle in order to follow the lane 190; if the reduced degree of attentiveness of the driver then still persists, a haptic warning to the driver can be initiated; if the reduced degree of attentiveness of the driver then still persists, a visual warning to other road users can be given by operating the hazard lights 105; if the reduced degree of attentiveness of the driver then still persists, a braking process for the vehicle can be initiated. The effect that can be achieved by this is that initially comparatively minor interventions are made in various operating parameters of the automobile 100; if the reduced degree of attentiveness persists, an intensity of the intervention in the various operating parameters of the automobile 100 can be increased so as in this way to restore a safe journey situation and an unreduced degree of attentiveness of the driver.

FIG. 2 shows sensors 220. The sensors 220 provide a control signal that indicates a journey situation parameter for the journey situation in which the driver finds himself and a steering parameter for steering of the vehicle 100. It would be possible for the period to continue to be determined on the basis of the journey situation parameter and/or the steering parameter and/or the lane parameter. The journey situation parameter can relate to a driving time; a time of day; an initiation frequency for a driver assistance system; a frequency for a change in a speed of the vehicle; and/or a frequency for the operation of pedals of the vehicle. The steering parameter can denote an accuracy with which the driver follows the lane 190; a time characteristic for operation of the steering of the automobile 100; a steering angle; a characteristic of the steering angle; a steering angle speed; and/or a steering torque. The lane parameter can denote a period before a lane marker is crossed and/or a distance to a lane marker.

Such aforementioned journey situation parameters and steering parameters and lane parameters may, taken individually, be indicative of the degree of attentiveness of the driver. Additional consideration of these various journey situation parameters and/or steering parameters and/or lane parameters allows particularly accurate monitoring of the degree of attentiveness to be achieved. In particular, it may be possible for the degree of attentiveness to be determined in a manner particularly concordant with the situation. It would be possible for the period to be determined as being longer (shorter) when the driving time is shorter (longer); the time is during the day (night time); driver assistance systems initiate comparatively rarely (comparatively frequently); the speed 101 is altered comparatively frequently (rarely); the pedals are operated comparatively frequently (rarely); or the ambient brightness is high (low).

A comparatively long (short) period will thus be determined when high (low) level of activity of the driver is detected by means of the journey situation parameters and/or the steering parameters. In summary, particularly accurate determination of the degree of attentiveness of the driver can be achieved by the by sensor fusion techniques.

Figure 3:
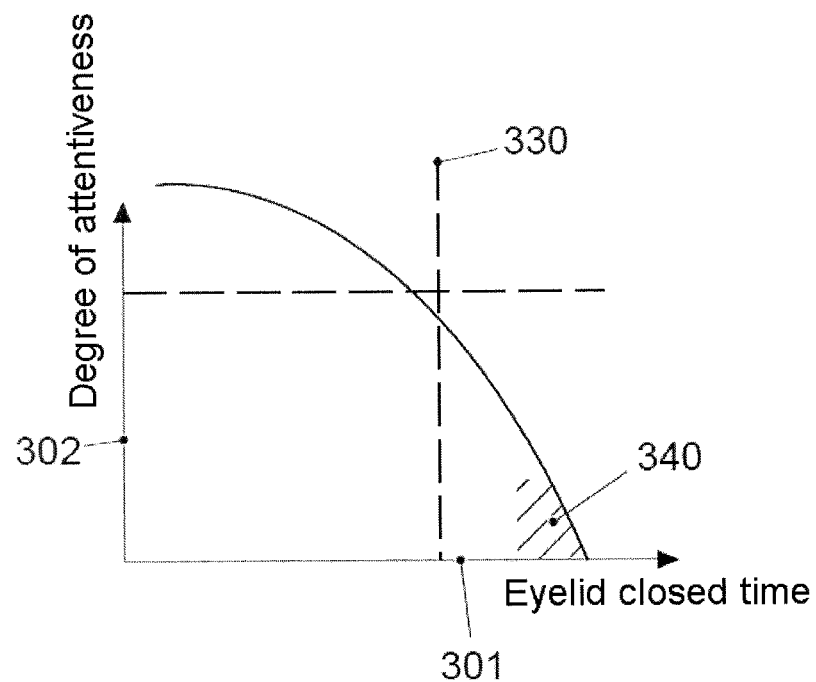
FIG. 3 illustrates a degree of attentiveness of the driver on the basis of an eyelid closed time of the driver, with a reduced degree of attentiveness being assumed when the eyelid closed time exceeds a particular period.

FIG. 3 plots a quantification of the degree of attentiveness 302 as a function of eyelid closed time 301 by way of example. A vertical dashed line illustrates the period 330 in FIG. 3. When the eyelid closed time exceeds the period 330, a reduced degree of attentiveness 302 can be assumed. When the degree of attentiveness 302 is particularly reduced, microsleep 340 can be assumed (shown by shading in FIG. 3).

Instead of the eyelid closed time 301, the eyelid closing time could also be considered in FIG. 3. In that case, the period 330 would possibly need to be chosen to be shorter; this is the case because typically comparatively short eyelid closing times indicate a reduced degree of attentiveness.

Figure 4:
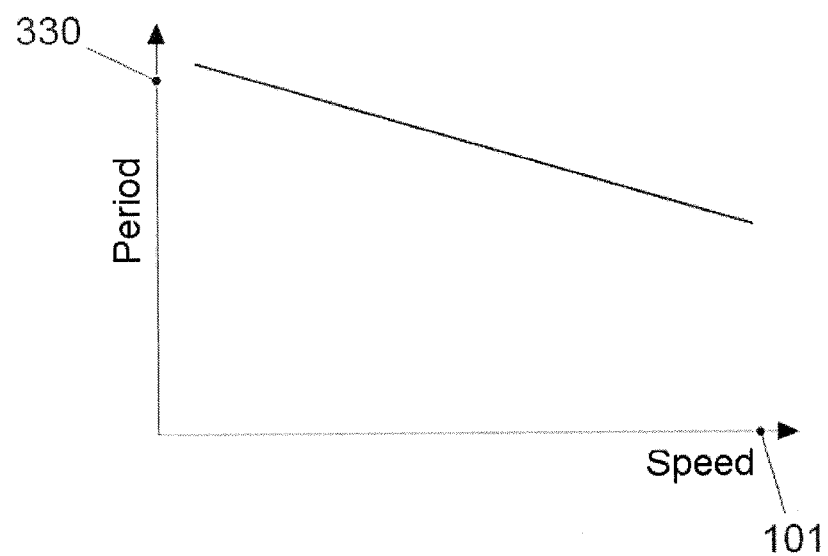
FIG. 4 illustrates a dependency of the period on a speed of the vehicle.

The period 330 can be determined as a function of the speed 101 of the automobile 100 (cf. FIG. 4). Higher (lower) speeds 101 can correspond to shorter (longer) periods 330. Alternatively or additionally, it would also be possible for the period 330 to be determined on the basis of the journey situation parameter and/or on the basis of the steering parameter and/or the lane parameter.

Figure 5:
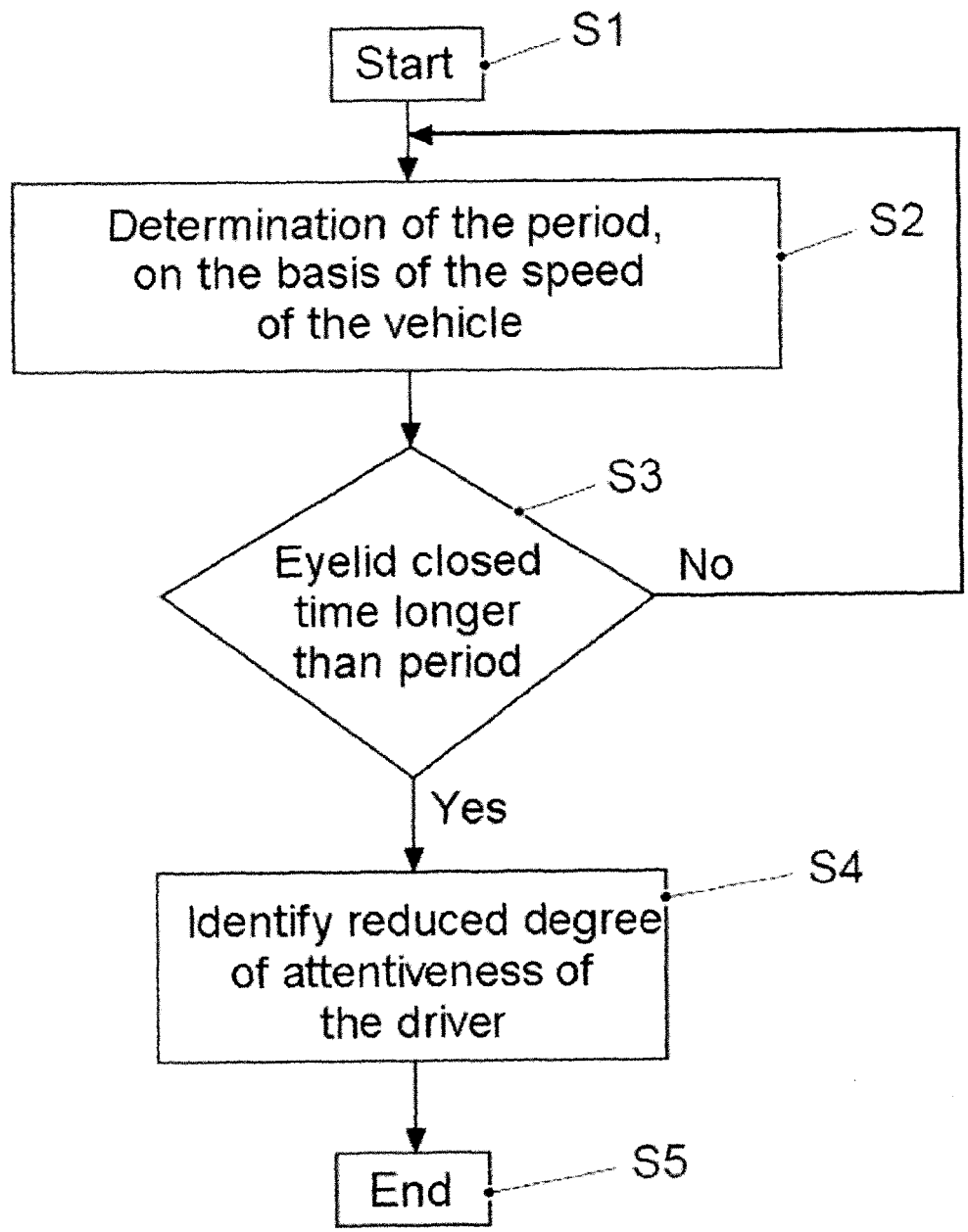
FIG. 5 is a flowchart for a method for monitoring a degree of attentiveness for the driver of the vehicle.

FIG. 5 shows a flowchart of a method for monitoring the degree of attentiveness of the driver according to various disclosed embodiments. The method begins in step S1. First of all, step S2 involves the period 330 being determined on the basis of the speed 101 of the automobile 100 (cf. FIG. 4). Next, step S3 involves determination of whether the eyelid closed time is longer than the period 330 (cf. FIG. 3). The eyelid closed time 301 can be ascertained from the image data 120a that are received from the interior camera 120. If the eyelid closed time 301 is longer than the period 330, step S4 involves the reduced degree of attentiveness of the driver being identified. It is then possible to warn the driver by means of the driver warning device 250 and to initiate a driver assistance action by means of the driver assistance system 260. It is possible for various warnings and/or various driver assistance actions to be initiated progressively, depending on the length of time for which the reduced degree of attentiveness of the driver persists or on the basis of whether microsleep 340 is identified. In particular, it is possible to check in this context whether the eyelid of the driver continues to be closed or is opened again.

The method ends in step S5.

It goes without saying that the features of the embodiments that have been described above can be combined with one another. In particular, the features can be used not only in the combinations described but also in other combinations or on their own without departing from the scope and field of the disclosure.

Reference has been made above primarily to the eyelid closed time. However, it would alternatively or additionally be possible for the monitoring of the degree of attentiveness also to be performed taking into consideration the eyelid closing time.

Techniques are known in which a steering behavior and a driving time of a driver of a motor vehicle are taken as a basis for checking whether the degree of attentiveness of the driver is restricted. However, it may happen that the steering behavior in conjunction with the driving time are not sufficiently accurate for safe and reliable monitoring of the degree of attentiveness. This can result in dangerous situations for the driver or for other road users. Particularly when there is support by one or more driver assistance systems, the degree of attentiveness may be reduced. In connection with automatic driving techniques, the degree of attentiveness of the driver may be reduced to a particularly great extent. However, even in scenarios in which the driver is extensively supported by one or more driver assistance systems, it may be desirable for the driver to provide an adequate degree of attentiveness.

Techniques that involve monitoring a period for which an eyelid of the driver is closed (eyelid closed time) of the driver are also known. The eyelid closed time can thus denote the period for which the eyelid remains in the closed state. In this way, it is possible to detect a microsleep by the driver and to determine the degree of attentiveness comparatively accurately as a result.

Such techniques are comparatively inflexible, however. It may happen that a reduced degree of attentiveness is determined on the basis of an extended eyelid closed time, even though the driver musters appropriate or situation-concordant attentiveness toward the journey situation.

There is therefore a need for improved techniques for monitoring the degree of attentiveness of the driver. In particular, there is a need for techniques that allow flexible and situation-concordant monitoring of the degree of attentiveness. In particular, there is a need for techniques for monitoring the degree of attentiveness that are able to identify a microsleep by the driver.

LIST OF REFERENCE SYMBOLS

100 Vehicle
101 Speed of the vehicle
105 Hazard lights
120 Interior camera
121 Field of view of the interior camera
120a Image data
190 Lane
200 Controller
201 Computation unit
202 Interface
220 Sensors
250 Driver warning device
260 Driver assistance system
301 Eyelid closed time
302 Degree of attentiveness
330 Period
340 Microsleep
S1-S5 Method step

The invention claimed is:

1. A method for monitoring a degree of attentiveness for a driver of a vehicle, the method comprising:
   determining a period based on a speed of the vehicle;
   receiving image data from an interior camera that depict a portion of the face of the driver;
   determining whether a blink time of the driver exceeds the determined period based on the image data and identifying a reduced degree of attentiveness when the blink time of the driver exceeds the period;
   monitoring the degree of attentiveness of the driver based on the determination of whether the blink time exceeds the period,
   wherein the method is executed by a controller that is preconfigured to carry out the method.

2. The method of claim 1, further comprising:
   obtaining a control signal that indicates at least one of a journey situation parameter for a journey situation in which the driver finds himself, a steering parameter for steering and a lane parameter for the vehicle,
   wherein the determination of the period is additionally based on the control signal obtained.

3. The method of claim 2, wherein the journey situation parameter is selected from the group comprising: a driving time; a time of day; an initiation frequency for a driver assistance system; a frequency for a change in the speed of the vehicle; a frequency for operation of pedals of the vehicle; and ambient brightness.

4. The method of claim 2, wherein the steering parameter is selected from the group comprising: an accuracy with which the driver follows a lane; a time characteristic for operation of the steering of the vehicle; a steering angle; a characteristic for the steering angle; a steering angle speed; and a steering torque; and/or wherein the lane parameter is selected from the group comprising: a period before a lane marker is crossed and a distance to a lane marker.

5. The method of claim 1, further comprising:
   output of an audible warning and/or a haptic warning to the driver when the result of the monitoring is a reduced degree of attentiveness of the driver.

6. The method of claim 1, wherein a driver assistance system of a vehicle outputs a driver assistance action when the result of the monitoring is a reduced degree of attentiveness of the driver.

7. The method of claim 6, wherein the driver assistance action is initiated when the reduced degree of attentiveness of the driver persists for a prescribed further period.

8. The method of claim 6, further comprising successive initiation of at least two driver assistance actions if the reduced degree of attentiveness persists,
   wherein the at least two driver assistance actions are selected from the group comprising: lateral guidance of the vehicle to follow a lane lateral guidance of the vehicle to reach a breakdown lane; braking of the vehicle; and operation of hazard lights of the vehicle.

9. A controller that monitors a degree of attentiveness for a driver of a vehicle, wherein the controller comprises:
   an interface, wherein the interface is set up to receive image data that depict a portion of the face of the driver; and
   a computation unit, wherein the computation unit is set up to determine a period based on a speed of the vehicle, wherein the computation unit is additionally set up determine whether a blink time of the driver exceeds the determined period based on the image data,
   wherein the computation unit is additionally set up to monitor the degree of attentiveness of the driver based on the determination of whether the blink time exceeds the period.

10. The controller of claim 9, wherein the controller is set up to perform a method comprising:
    determining a period based on a speed of the vehicle;
    receiving image data that depict a portion of the face of the driver;
    determining whether a blink time of the driver exceeds the period based on the image data; and
    monitoring the degree of attentiveness of the driver based on the determination of whether the blink time exceeds the period.

* * * * *